(12) United States Patent
Kabus et al.

(10) Patent No.: US 8,798,343 B2
(45) Date of Patent: Aug. 5, 2014

(54) SYSTEM FOR PROVIDING LUNG VENTILATION INFORMATION

(75) Inventors: Sven Kabus, Hamburg (DE); Cristian Lorenz, Hamburg (DE); Nicole Schadewaldt, Hamburg (DE); Roland Opfer, Hamburg (DE); Ingwer Curt Carlsen, Hamburg (DE); Steffen Renisch, Hamburg (DE); Joerg Sabczynski, Norderstedt (DE); Hans Barschdorf, Dassendorf (DE); Jens Von Berg, Hamburg (DE); Thomas Blaffert, Hamburg (DE); Tobias Klinder, Uelzen (DE)

(73) Assignee: Koninklijke Philips N.V., Eindhoven (NL)

( * ) Notice: Subject to any disclaimer, the term of this patent is extended or adjusted under 35 U.S.C. 154(b) by 202 days.

(21) Appl. No.: 13/146,885

(22) PCT Filed: Jan. 25, 2010

(86) PCT No.: PCT/IB2010/050305
§ 371 (c)(1),
(2), (4) Date: Jul. 28, 2011

(87) PCT Pub. No.: WO2010/086776
PCT Pub. Date: Aug. 5, 2010

(65) Prior Publication Data
US 2011/0286652 A1    Nov. 24, 2011

(30) Foreign Application Priority Data

Jan. 30, 2009 (EP) .................................... 09151764

(51) Int. Cl.
*G06K 9/00* (2006.01)
(52) U.S. Cl.
USPC ............ 382/128; 378/65; 382/130; 382/131; 382/218; 600/410; 600/420; 600/427; 600/534

(58) Field of Classification Search
None
See application file for complete search history.

(56) References Cited

U.S. PATENT DOCUMENTS 5,790,690 A * 8/1998 Doi et al. ...................... 382/128
6,501,981 B1 * 12/2002 Schweikard et al. ......... 600/427

(Continued)

FOREIGN PATENT DOCUMENTS

JP    2005028121 A    2/2005
WO    2005112757 A2    12/2005

(Continued)

OTHER PUBLICATIONS

Thomas Guerrero et al.: "Dynamic Ventilation Imaging From Four-Dimensional Computed Tomography; Dynamic Ventilation Imaging" Physics in Medicine and Biology, Taylor and Francis Ltd. London, GB; vol. 51, No. 4, Feb. 21, 2005, pp. 777-791.

(Continued)

*Primary Examiner* — Tsung-Yin Tsai (57) ABSTRACT

A system for displaying lung ventilation information, the system comprising an input (12) and a processing unit (15). The input being provided for receiving multiple CT images (71) of a lung, each CT image (71) corresponding to one phase of at least two different phases in a respiratory cycle. The processing unit (15) being configured to compare CT images (71) corresponding to different phases in the respiratory cycle for determining a deformation vector field for each phase, to generate for each phase a ventilation image (72) based on the corresponding deformation vector field, to spatially align the ventilation images (72), and to generate for at least one common position (62) in each one of the aligned ventilation images (72), a function (81) of a time course of a ventilation value for said common position (62), each ventilation value in the function (81) being based on the deformation vector fields corresponding to the aligned ventilation images (73).

13 Claims, 9 Drawing Sheets

(56) References Cited

U.S. PATENT DOCUMENTS

| | | | |
|---|---|---|---|
| 7,106,891 B2* | 9/2006 | Wyman et al. | 382/128 |
| 7,286,694 B2* | 10/2007 | Oosawa | 382/128 |
| 7,393,329 B1* | 7/2008 | Wong et al. | 600/534 |
| 7,668,357 B2* | 2/2010 | Keall et al. | 382/130 |
| 7,903,849 B2* | 3/2011 | Kimura | 382/128 |
| 2001/0048757 A1* | 12/2001 | Oosawa | 382/130 |
| 2002/0198449 A1* | 12/2002 | Baumgardner et al. | 600/420 |
| 2004/0258286 A1* | 12/2004 | Salla et al. | 382/128 |
| 2005/0025365 A1* | 2/2005 | Oosawa | 382/218 |
| 2005/0226485 A1* | 10/2005 | Boese | 382/131 |
| 2006/0165267 A1* | 7/2006 | Wyman et al. | 382/128 |
| 2006/0264736 A1* | 11/2006 | Ehman et al. | 600/410 |
| 2007/0086636 A1* | 4/2007 | Keall et al. | 382/131 |
| 2009/0041188 A1* | 2/2009 | Keall et al. | 378/65 |
| 2009/0208081 A1* | 8/2009 | Saha et al. | 382/131 |
| 2010/0014736 A1* | 1/2010 | Barschdorf et al. | 382/131 |
| 2010/0061606 A1* | 3/2010 | Geiger et al. | 382/128 |

FOREIGN PATENT DOCUMENTS

| | | | | |
|---|---|---|---|---|
| WO | 2009132002 A1 | 10/2009 | | |
| WO | WO 2009132002 A1 * | 10/2009 | | A61B 5/08 |

OTHER PUBLICATIONS

Yaremko et al. : "Reduction of Normal Lung Irradiation in Locally Advanced Non-Small-Cell Lung Cancer Patients, Using Ventilation Images for Functional Avoidance" International Journal of Radiation Oncology Biolgy Physics, Pergamon Press USA, vol. 68, No. 2 May 9, 2007 pp. 562-571.

* cited by examiner

SYSTEM FOR PROVIDING LUNG VENTILATION INFORMATION

FIELD OF THE INVENTION

This invention relates to a system for displaying lung ventilation information, the system comprising an input for receiving multiple CT images of a lung, each CT image corresponding to one phase of at least two different phases in a respiratory cycle, and a processing unit configured to:
compare CT images corresponding to consecutive phases for determining a deformation vector field for each phase,
generate, for each phase, a ventilation image based on the corresponding deformation vector field, and
spatially align the ventilation images,
and further comprising a display for displaying lung ventilation information.

This invention further relates to a method of displaying lung ventilation information and to a computer program product.

BACKGROUND OF THE INVENTION

Japanese patent application JP 2005-028121 describes a system for measuring local lung ventilation. Said system uses a 3D CT scan of the lungs at the moments of inhalation and exhalation. The inhalation image and the exhalation image are then aligned and a displacement vector field is obtained. Local lung ventilation is computed from the displacement vector field. Integration of local values is performed for obtaining a total ventilation amount. FIG. 3 of JP 2005-028121 shows a picture wherein the local lung ventilation is visualized. In this picture, areas of expansion, areas of contraction and areas having a constant volume are indicated.

It is a problem of the system of JP 2005-028121 that the output picture only provides information about the local volume change for a complete breathing cycle. More detailed information may help a doctor, therapist or researcher to make a better assessment of the physical condition of an examined lung.

OBJECT OF THE INVENTION

It is an object of the invention to enable improved assessment of local lung ventilation.

SUMMARY OF THE INVENTION

According to a first aspect of the invention, this object is achieved by providing a system for displaying lung ventilation information, the system comprising an input and a processing unit. The input is provided for receiving multiple CT images of a lung, each CT image corresponding to one phase of at least two different phases in a respiratory cycle. The processing unit is configured to: compare CT images corresponding to different phases in the respiratory cycle for determining a deformation vector field for each phase, generate, for each phase, a ventilation image based on the corresponding deformation vector field, spatially align the ventilation images, and generate, for at least one common position in each one of the aligned ventilation images, a function of a time course of a ventilation value for said common position, each ventilation value in the function being based on the deformation vector fields corresponding to the aligned ventilation images. A display may be provided for displaying at least one of the ventilation or CT images and a diagram of the generated function.

By computing the local ventilation, for each phase transition the degree of contraction or expansion can be delivered to the physician. The amount of ventilation can be delivered for any user-chosen position in the lung and for any moment during a breathing cycle, rather than as a global amount for a complete breathing cycle. This system makes it possible to display relevant information in all spatial dimensions (2D or 3D) and simultaneously display information in a temporal dimension. The displayed ventilation images show a lung ventilation distribution for the imaged region, while the diagram or diagrams show the time course of the local ventilation at one or more specific positions or regions. The positions or regions may be selected automatically or by user interaction. For example, a tumor region or a reference region with healthy tissue may be selected. With the system according to the invention, not only a comparison of max-inhale and max-exhale state can be performed, but any two phases can be compared, yielding a temporal measurement of local lung ventilation. It is to be noted that even if the ventilation computed for the transition from maximum inhalation to maximum exhalation is the same at two different positions or for two patients, the phase-to-phase ventilation may be different. The information from all phase-to-phase ventilation images provides a better tool for early cancer diagnosis. In an embodiment of the system according to the invention, a respiratory cycle model is fitted to the generated function. The fitted model may be displayed together with the generated function in order to visualize the differences between the theoretical model and the measured ventilation profile. Moreover, the parameters used for fitting the respiratory cycle model to the generated function may hold useful information such as ventilation amplitude or ventilation phase shift. If such parameters are determined for different positions in the lung, they may be visualized in a lung atlas showing the parameter values at corresponding positions, e.g. using color coding.

In a further embodiment of the system according to the invention, the ventilation profile is determined multiple times, e.g. during a course of a treatment. The multiple generated functions may then be used for a trend analysis. The trend analysis may result in displaying a sequence of ventilation profiles. Preferably, the trends of important parameters such as the ventilation amplitude and/or the ventilation phase shift are calculated and displayed.

It is also possible to determine the ventilation profile for multiple patients and to use the obtained data for creating a statistical model of functional lung data and to show the statistical data as a functional lung atlas.

Preferably, user input means are provided, which are coupled to the processing unit and enable a user to select the at least one common position in the displayed ventilation image. Using these input means, the doctor, physician or examiner has the opportunity to take a closer look at the local lung ventilation at a particular position of interest.

According to a second aspect of the invention, a method of displaying lung ventilation information is provided, the method comprising the steps of obtaining multiple CT images of a lung, each CT image corresponding to one phase of at least two different phases in a respiratory cycle, comparing CT images corresponding to different phases for determining a deformation vector field for each phase generating, for each phase, a ventilation image based on the corresponding deformation vector field, spatially aligning the ventilation images, generating, for at least one common position in each one of the aligned ventilation images, a diagram of a time course of a ventilation value for said common position, each ventilation value in the diagram being based on the deformation vector fields corresponding to the aligned ventilation images, and displaying at least one of the ventilation or CT images and the diagram.

According to a third aspect of the invention, a computer program product is provided for causing a processor to perform the method described above.

It will be appreciated by those skilled in the art that two or more of the above-mentioned embodiments, implementations, and/or aspects of the invention may be combined in any way deemed useful.

Modifications and variations of the system, of the method, of the image acquisition apparatus, of the workstation, and/or of the computer program product, which correspond to the described modifications and variations of the system or the method, can be carried out by a person skilled in the art on the basis of the present description.

These and other aspects of the invention are apparent from and will be elucidated with reference to the embodiments described hereinafter.

DETAILED DESCRIPTION OF THE INVENTION

Figure 1:
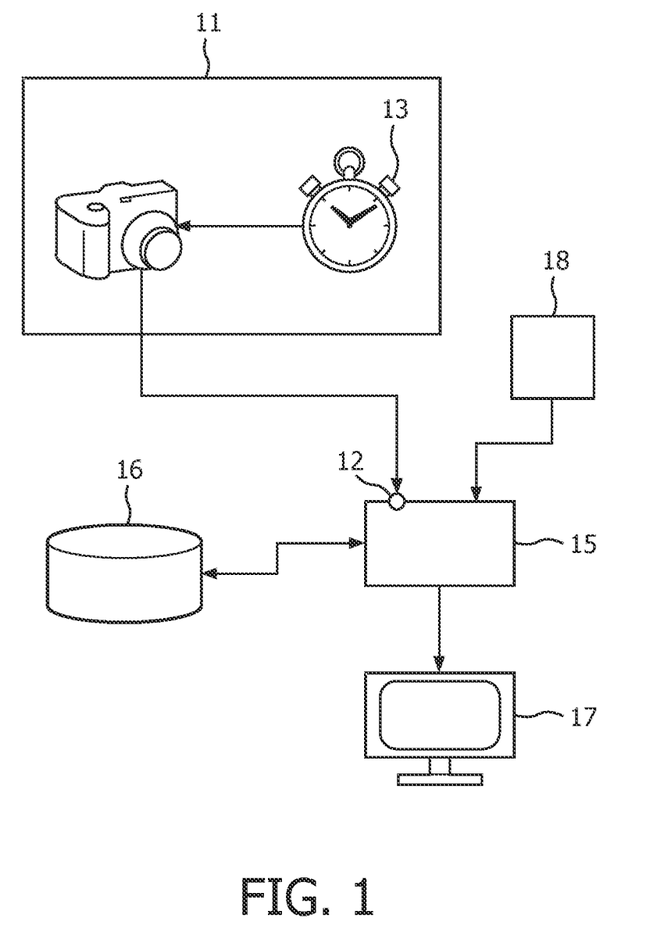
FIG. 1 schematically shows a system according to the invention.

FIG. 1 schematically shows a system according to the invention. The system comprises a processor unit 15 with an input 12 for obtaining CT images of a lung. The CT images are obtained by a CT scanner 11, which may be part of or coupled to the system. A time stamp is added to the images obtained by the CT scanner 11. During the CT scan, patient respiratory traces are acquired with a marker block placed on, e.g., the upper abdomen. The projection images are retrospectively sorted into, e.g., ten respiratory phase-based bins of 3D CT image data (i.e., from 0% to 90% phase at 10% intervals). The time stamps are added by, e.g., an internal clock 13 of the CT scanner 11. The processing unit 15 may store the obtained images on a storage means 16, e.g. a hard disk. The images may be processed immediately upon receipt, or may be retrieved from the storage means 16 at a later point of time for being processed. The processing results in the generation of diagrams showing time courses of local lung ventilation at a certain location in the examined lung. After processing of the CT images, a display 17 will show a lung ventilation image and one or more of the generated diagrams. The processing of the CT images will be discussed below with reference to FIG. 2. User input means 18 may be provided for enabling a user to control the processing and/or to select display modes and display options.

Figure 2:
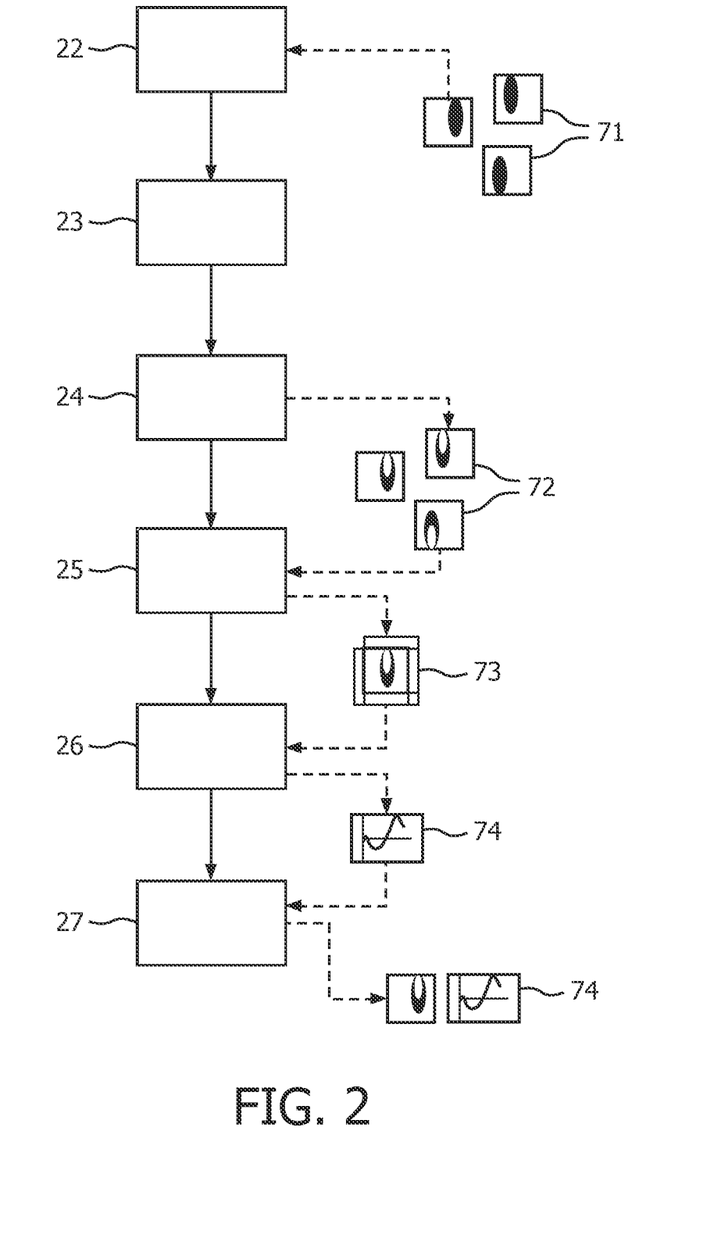
FIG. 2 shows a flow diagram of a method according to the invention.

FIG. 2 shows a flow diagram of a method according to the invention. In input step 22, the CT images 71 are received at the input 12 of the system. The CT images 71 represent at least part of a lung. CT images 71 are obtained at different moments in the respiratory cycle of a patient. Preferably, about ten images 71 are obtained per breathing cycle, resulting in a subdivision of the breathing cycle in ten different phases, varying from maximum exhalation to maximum inhalation and comprising phases in between. By acquiring images at different depths, a 3D image 71 may be obtained for each phase.

In comparison step 23, images 71 of consecutive phases are compared using pattern recognition and/or image registration algorithms. The differences between the images 71 of two consecutive phases are stored in, e.g., a deformation vector field. It is to be noted that differences between images 71 of two consecutive phases may result either from the breathing motion or from movements of the examined subject as a whole. Because movements of the patient as a whole are more or less equal for all parts of the lung, the registered differences between two images 71 may be compensated for such movements. Instead of comparing images 71 of consecutive phases, it is also possible to compare each phase to, e.g., one reference phase.

Figure 5:
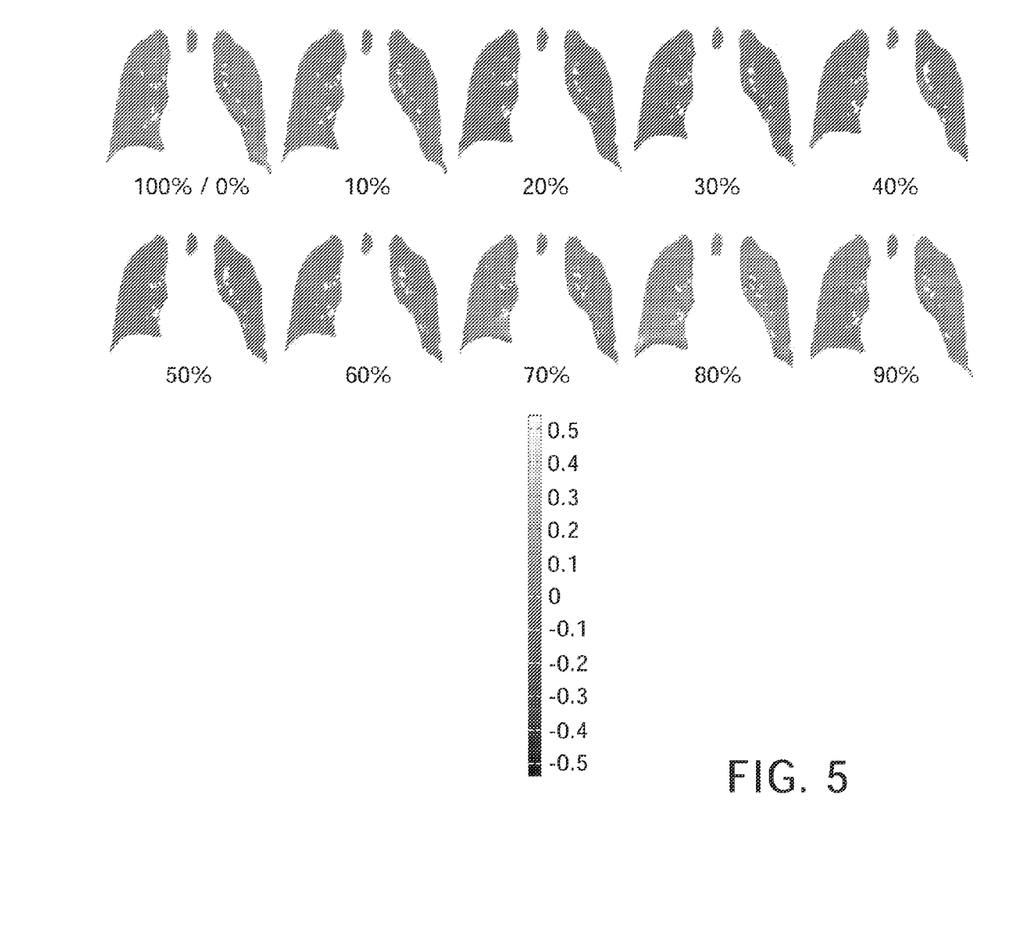
FIG. 5 shows a series of lung ventilation images derived from the deformation vector fields of FIG. 4.

In ventilation-determining step 24, the deformation vector fields are used to compute ventilation images 72. Ventilation describes air intake. Higher ventilation values correspond to higher air intake measured, for examples, in L/min. the ventilation may be computed by, e.g., computing the divergence of the deformation vector fields or the determinant of the Jacobian of the deformation vector fields or by taking a Hounsfield value from a chosen phase and a Hounsfield value from a deformed other phase which correspond due to the computed deformation vector field followed by a computation of the relative change. For each phase a ventilation image 72 is generated. Exemplary ventilation images 72 are shown in FIG. 5. The ventilation images 72 show for each phase and for each location in the observed lung whether the lung tissue is locally expanding or contracting. A ventilation offset is chosen such that the value of 0 corresponds to no air intake.

In alignment step 25, the ventilation images 72 are aligned. One of the ventilation images 72 is used as a reference image. For example, the maximum inhalation state may be used as the reference phase. The other ventilation images 72 are shifted in such a way that non-moving reference points in the imaged area are at the same position in each one of the aligned images 73. The reference points may be indicated by the user in all images. Alternatively, the user indicates one reference point in one image and the processing unit 15 automatically searches for the corresponding points in images corresponding to different phases. Also the one reference point to be searched for may be found by the processing unit, using a search algorithm and some predefined searching criteria. As a result, each ventilation image 72 is defined in the coordinate system of the reference phase, whereas before alignment the i-th ventilation image was associated with the coordinate system belonging to the i-th phase. The alignment of the images may alternatively be performed before the generation of the deformation vector fields. In that event, the CT images 71 are aligned and alignment of the ventilation images 72 is not needed anymore. In both cases, the eventual result will be a set of aligned ventilation images 73.

In diagram generation step 26 at least one diagram is generated for showing a time course of the ventilation value for a particular position in the examined lung. For this purpose, the lung ventilation at different phases may be analyzed for one or more standard positions. Alternatively, the user may select one or more positions for which he would like to see the time course of the lung ventilation.

Figure 3:
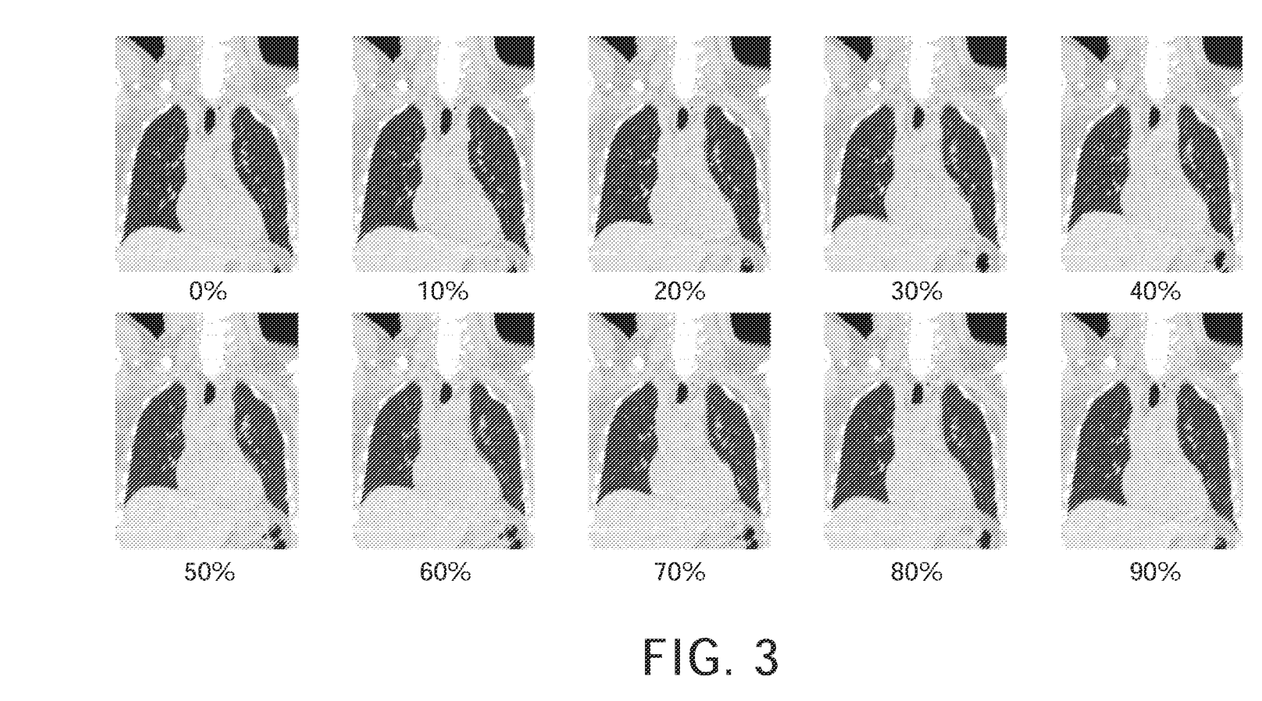
FIG. 3 shows a series of CT images of a pair of lungs.

FIG. 3 shows a series of CT images 71 of a pair of lungs. In this Figure ten images are shown, each image representing a different phase in the respiratory cycle. Although it may not yet be very clear from the CT images 71, in this event the 0% phase corresponds to the maximum inhalation state, the 10%, 20%, 30% and 40% states represent phases during the exhalation. The 50% state represents a transition from exhalation to inhalation. From 60% to 90%, the lungs are expanding because of inhalation. At maximum inhalation the breathing cycle is completed and the lungs are in the 0% state again. It is to be noted that in principle any moment in the breathing cycle may be defined as the 0% state. A good alternative for the maximum inhalation state may be the maximum exhalation state. In this example, there are roughly 5 exhalation states and 4 inhalation states. For other patients, or for other measurements of the same patient, the ratio of inhalation phases versus exhalation phases may differ.

Figure 4:
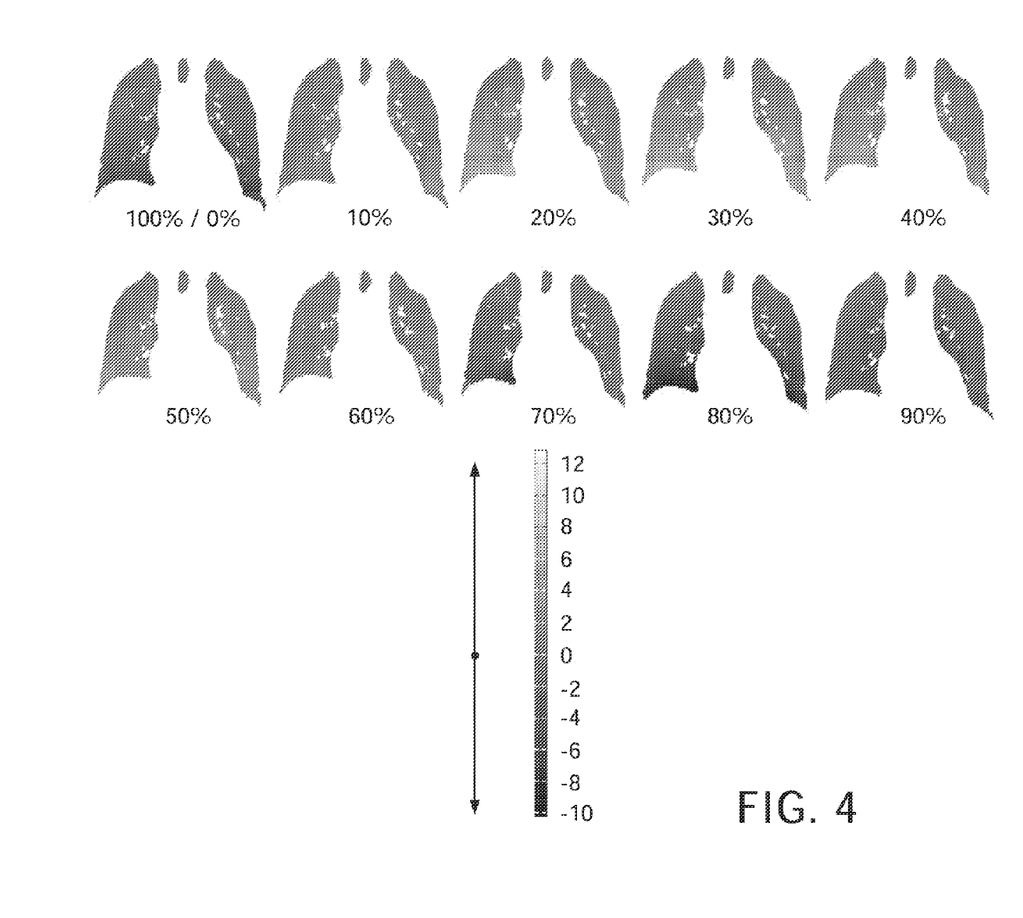
FIG. 4 shows a series of deformation vector field derived from the CT images of FIG. 3.

FIG. 4 shows a series of deformation vector fields derived from the CT images 71 of FIG. 3. In this example, the inferior-superior component is displayed. For each phase a measure of displacement in the inferior-superior direction is determined.

Preferably, the displacement is measured in 3 directions (x, y, z) to be able to perform a 3D analysis of the lung ventilation. The displacement is determined using pattern recognition algorithms. In the 10%-50% phases, most displacement is in an upward direction. Lighter areas in the picture represent larger displacements than darker areas. These five phases represent the exhalation phase in the breathing cycle. Exhalation is mainly caused by relaxation of the breathing musculature and the upward movement of the diaphragm, which results in the lung tissue being pushed upward and air being pushed out of the lungs. In the 60%-100%/0% phases, inhalation results in a downward displacement of lung tissue. Here, darker areas represent larger displacements. The downward moving diaphragm causes air to be sucked into the lungs. It may be advantageous to use color coding for indicating the amount and direction of displacement.

FIG. 5 shows a series of lung ventilation images 72 derived from the deformation vector fields of FIG. 4. These images 72 show, for each position in the examined lung, an expansion/contraction value. E.g., a value of 0 is associated with volume preservation, whereas a value below (above) 0 indicates contraction (expansion) which may be displayed by different colors.

Figure 6:
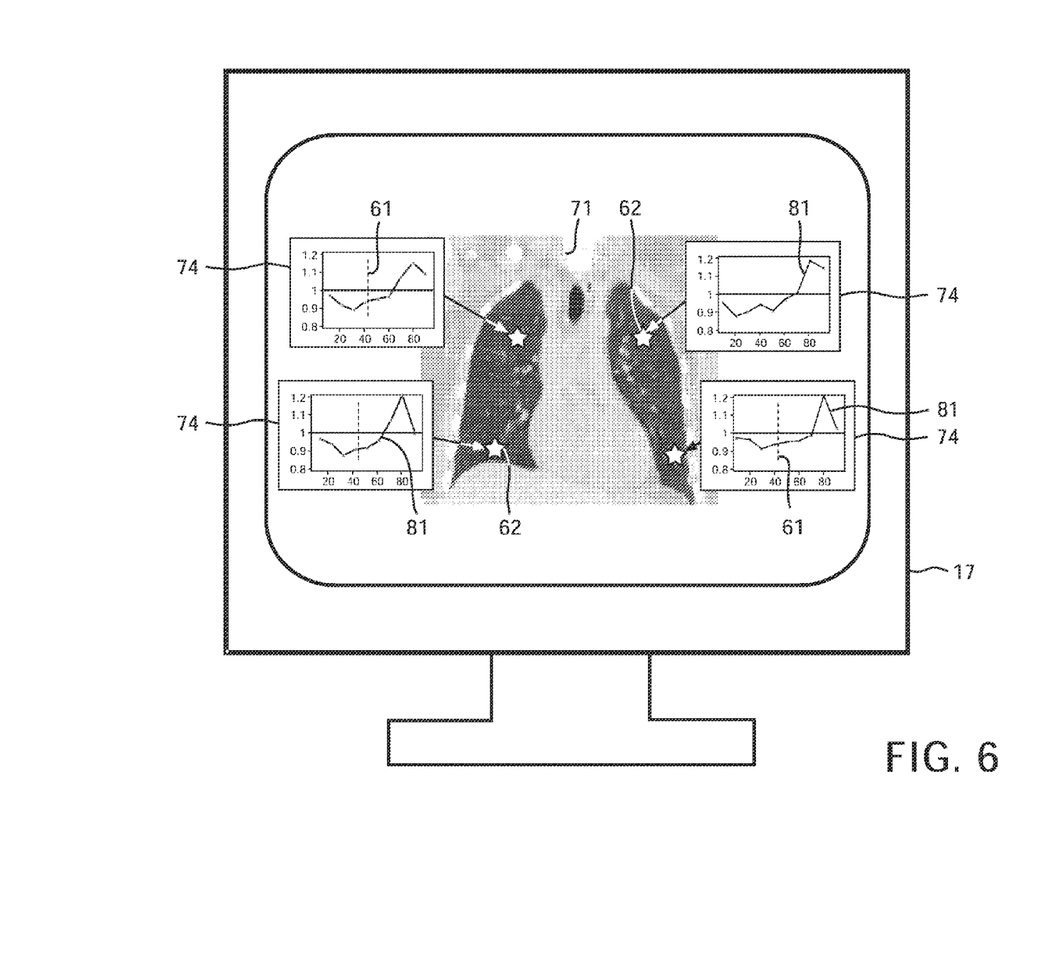
FIG. 6 shows an exemplary display of the system according to the invention.

FIG. 6 shows an exemplary display 17 of a system according to the invention. On the display 17, one of the CT images 71 is shown. The CT image 71 shows two lungs. The CT image shown represents one of the phases in the breathing cycle. A user interface may be provided for allowing a user to select an image 71 representing a different phase. Alternatively, two or more images 71 may be shown simultaneously. Instead of a CT image 71, also a ventilation image 72 may be shown. For four positions 62 in the CT image 71, the corresponding diagram 74 is displayed. The diagram 74 shows a time course of the ventilation value for the corresponding position 62. The ventilation offset is such that during exhalation, the ventilation value is below 1, and during inhalation, the ventilation value is above 1. The ventilation value is indicative of the lung volume. By clicking on positions in the CT image, the user may call the diagrams 74 showing the ventilation values for the corresponding positions. Optionally, the displayed diagrams 74 may show an indication 61 of the phase of the currently displayed CT image 71, such that the user sees what point in the diagram corresponds to the displayed image 71. By manipulating such indication 61, the user may select CT images of other phases to be displayed instead of selecting CT images to be displayed in addition to the currently displayed one.

Figure 7:
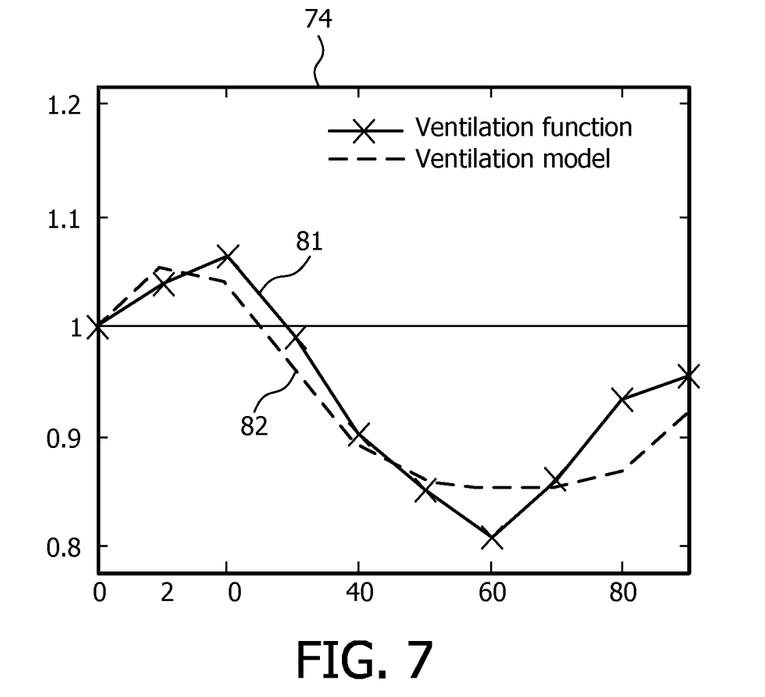
FIG. 7 shows a diagram of a generated ventilation function, together with a fitted respiratory cycle model.

FIG. 7 shows a diagram 74 of a generated ventilation function 81, together with a fitted respiratory cycle model 82. The respiratory cycle model 82 is a mathematical representation of the lung ventilation as a function of time. For example, the respiratory cycle model 82 may by defined as $$V(t)=V_0+b\cos^{2n}(c_1(t-\phi)+c_2),$$

wherein:
 $c_1$ is defined by the length of the respiratory cycle
 $c_2$ is an initial ventilation phase shift, at $t=\phi$,
 $V_0$ is an offset of the ventilation,
 b is a ventilation amplitude,
 $\phi$ is a reference time, and
 a typical value for n is 1.

Various models 82 may be suitable for fitting to a measured parameter. The choice of a mathematical model 82 may depend, e.g., on the measured parameter and/or the desired fitting accuracy. Parameter values of fitted models 82 may be calculated and displayed for selected positions in the lung area. Such parameters of the fitted model may comprise information useful for the person operating the system. For example, the ventilation amplitude and the ventilation phase shift may hold valuable information for assessing the physical state of the corresponding lung area.

Figure 8:
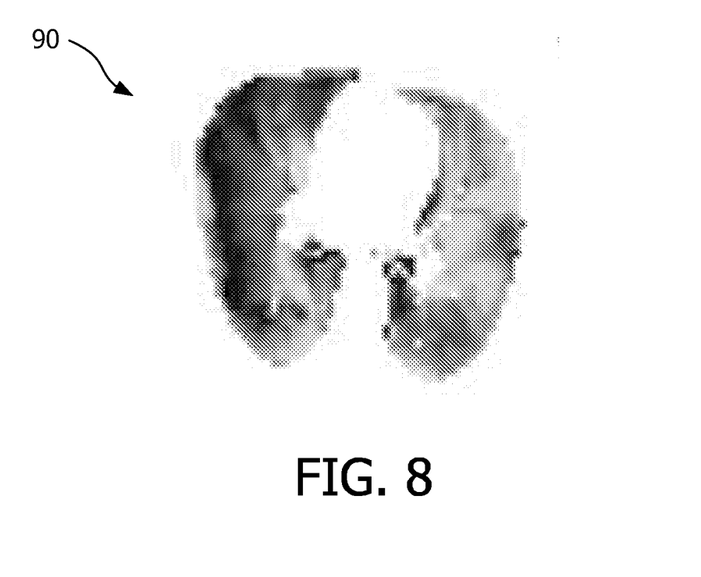
FIG. 8 shows an exemplary lung atlas.

A lung atlas 90 may be computed and displayed to visualize values of a parameter of the fitted model 82 at a plurality of positions in the lung. For example, a color coded image of the lung may show the ventilation amplitudes or the ventilation phase shift at clinically relevant positions in the lung image. FIG. 8 shows an exemplary lung atlas 90, wherein each pixel corresponds to a position in the lung at a certain moment in the respiratory cycle. The parameter is the ventilation amplitude. The color of each pixel indicates the value of the parameter. Such lung atlases may be generated also for other parameters and lung regions.

Figure 9:
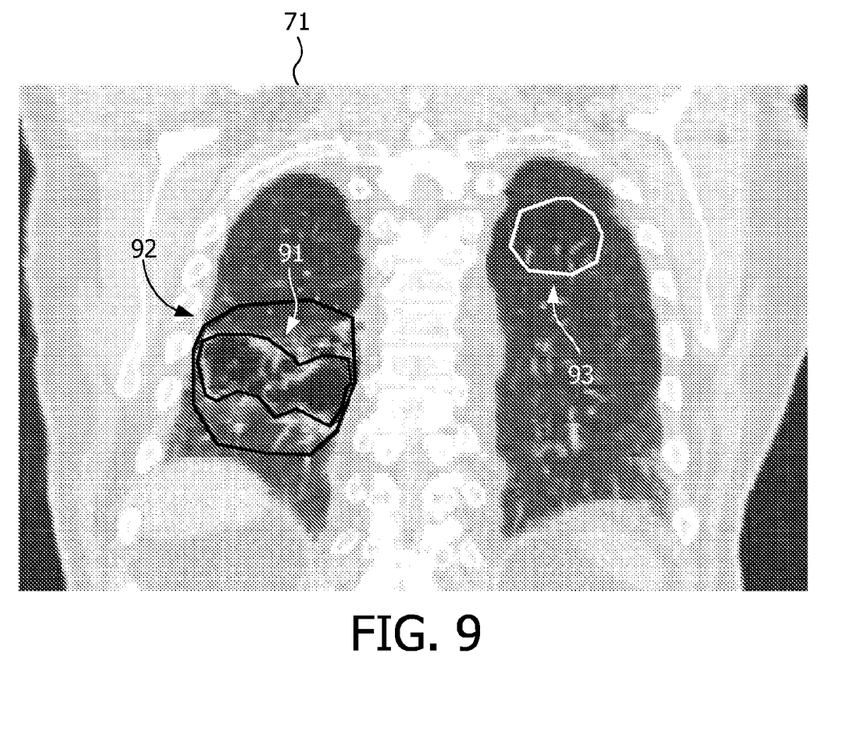
FIG. 9 shows a CT image of a lung in which image specific areas are highlighted.
Figure 10:
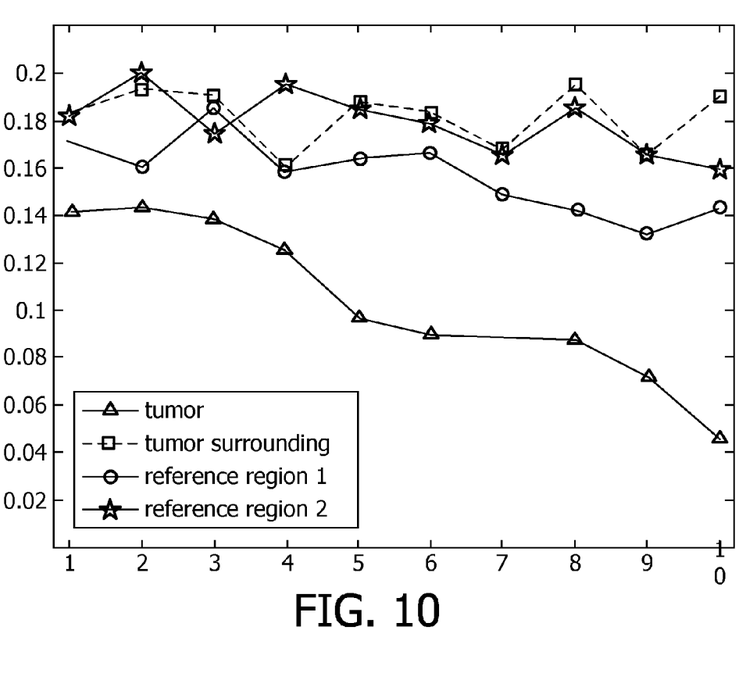
FIG. 10 shows a time course of a ventilation parameter over a period of ten weeks.

A lung atlas may show information about a change of a lung ventilation parameter over a period of time at selected positions in the lung. In such a lung atlas it is possible to show the development of the ventilation status, e.g. during treatment or due to progressing illness. Alternatively, a lung atlas may be generated using lung ventilation parameters of multiple patients. Such a lung atlas may provide statistical information about lung functioning in specific groups of patients. For example, a lung atlas may be provided for healthy people, smokers, non-smokers, people with lung cancer, etc. the displayed parameter value may be a population mean or standard deviation of a parameter. FIG. 9 shows a CT image 71 of a lung in which image specific areas 91, 92, 93 are highlighted. FIG. 10 shows a time course of a ventilation parameter in the highlighted areas 91, 92, 93 of FIG. 9 over a period of ten weeks. The specific areas 91, 92, 93 may be selected by a user. For example, the user interface of the system may allow the user to draw the selected areas with a pointing device, such as a mouse or joystick. In addition to the areas to be monitored, the user may also select one or more parameters to be monitored and/or the time scale of the monitoring diagram. The areas 91, 92, 93 may also be automatically selected using image recognition techniques. For example, the system may recognize and select the tumor area 91. A tumor surrounding area 92 is then selected around the tumor area 91. One or more reference regions 93 are found in the other lung or, at a distance from the tumor area, in the same lung. Preferably, the reference region 93 comprises only healthy lung tissue.

In FIG. 10, a lung ventilation parameter, the ventilation amplitude, is shown for the selected regions 91, 92, 93. The value of the lung parameter for each region may be a mean of all values in the region, a maximum value in the region, etc. It is to be noted that the graph may include ventilation parameters for regions which are not visible in the CT image of FIG. 9, e.g., because such regions are situated at a different depth. The graph in FIG. 10 shows that lung ventilation in the tumor area 91 declines during the ten weeks treatment, while the lung ventilation in the tumor surrounding area 92 only is only declining slightly and the lung ventilation in the reference regions 93 is substantially constant.

It will be appreciated that the invention also extends to computer programs, particularly computer programs on or in a carrier, adapted for putting the invention into practice. The program may be in the form of source code, object code, a code intermediate source and object code such as a partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one, a few, or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or stored in one or more files that may be linked statically or dynamically. Another embodiment relating to a computer program product comprises computer executable instructions corresponding to each of the means of at least one of the systems and/or products set forth. These instructions may be subdivided into subroutines and/or stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means. When the program is embodied in such a signal, the carrier may be constituted by such a cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for displaying lung ventilation information, the system comprising:
   an input for receiving multiple CT images of a lung, each CT image corresponding to one phase of at least two different phases in a respiratory cycle,
   a processing unit being configured to:
      compare CT images corresponding to different phases in the respiratory cycle for determining a deformation vector field for each phase,
      generate, for each phase, a ventilation image based on the corresponding deformation vector field,
      spatially align the ventilation images by selecting a reference ventilation image and shifting other ventilation images so that non-moving reference points are at the same position in each one of the aligned images,
      generate, for at least one common position in each one of the aligned ventilation images, a function of a time course of a ventilation value for said common position, each ventilation value in the function being based on the deformation vector fields corresponding to the aligned ventilation images.

2. A system as claimed in claim 1, wherein the processing unit is further configured to fit a respiratory cycle model to the function.

3. A system as claimed in claim 2, wherein the processing unit is further configured to derive a local ventilation amplitude and/or local ventilation phase shift from the fitted respiratory cycle model.

4. A system as claimed in claim 1, wherein the processing unit is further configured to generate the function multiple times, e.g. during a course of a treatment, and to make a trend analysis based on the multiple generated functions.

5. A system as claimed in claim 1, wherein the processing unit is further configured to generate the function for multiple subjects and to make a statistical analysis based on the multiple generated functions.

6. A system as claimed in claim 5, further comprising user input means, coupled to the processing unit, for enabling a user to select the at least one common position in the displayed ventilation or CT image.

7. A system as claimed in claim 1, further comprising a display for displaying at least one of the ventilation or CT images and a diagram of the function.

8. A system as claimed in claim 7, wherein the processing unit is configured to enable the user to use the user input means for selecting which one of the ventilation or CT images is to be displayed.

9. A system as claimed in claim 7, wherein the processing unit is configured to enable the user to select an alignment reference point in the displayed ventilation image and to spatially align the ventilation images with respect to the alignment reference point.

10. A system as claimed in claim 1, further comprising a CT scanner for obtaining the CT images.

11. A system as claimed in claim 1, further comprising a display for displaying, for each phase transition, a diagram showing the amount of local ventilation.

12. A method of displaying lung ventilation information, the method comprising the steps of:
- obtaining multiple CT images of a lung, each CT image corresponding to one phase of at least two different phases in a respiratory cycle,
- comparing CT images corresponding to different phases in the respiratory cycle for determining a deformation vector field for each phase,
- generating, for each phase, a ventilation image based on the corresponding deformation vector field,
- spatially aligning the ventilation images by selecting a reference ventilation image and shifting other ventilation images so that non-moving reference points are at the same position in each one of the aligned images,
- generating, for at least one common position in each one of the aligned ventilation images, a function of a time course of a ventilation value for said common position, each ventilation value in the function being based on the deformation vector fields corresponding to the aligned ventilation images.

13. A non-transitory computer readable memory to cause a processor to perform a method as claimed in claim 12.

* * * * *